United States Patent [19]

Witek et al.

[11] 4,283,399
[45] Aug. 11, 1981

[54] PARASTICIDE

[76] Inventors: Stanislaw Witek, Swobodna Str., 12; Damian Grobelny, Cieszkowskiego Str., 15, both of Wroclaw; Janina Ptaszkowska, Ks. Janusza Str., 62, Warszawa; Andrzej Bielecki, R. Luksemburg Str., 25, Opole; Edmund Bakuniak, Dzielna Str., 11a, Warszawa; Stefan Fulde, Traugutta Str., 7/9, Warszawa; Jadwiga Gorska-Poczopko, Instytucka Str., 4, Jablonna/k Warszawy, all of Poland

[21] Appl. No.: 42,407

[22] Filed: May 25, 1979

Related U.S. Application Data

[62] Division of Ser. No. 884,842, Mar. 9, 1978, Pat. No. 4,217,365.

[30] Foreign Application Priority Data

Mar. 11, 1977 [PL] Poland .................................. 196612

[51] Int. Cl.³ ............................................. A01N 43/84
[52] U.S. Cl. ............................. 424/248.4; 424/248.58; 544/162; 544/167
[58] Field of Search ........... 424/248.4, 248.57, 248.58; 544/108, 162, 167

*Primary Examiner*—Allen J. Robinson

[57] ABSTRACT

A parasiticide containing as an active ingredient the compound with the general formula 1, where:
  X is a halogen atom,
  Y is a hydroxyl, alkoxyl, alkyl or nitro group and "n" is the number of Y substituents and equals 0-4,
  $R^1$ is an alkyl radical with 1-3 carbon atoms or hydrogen atom,
  $R^2$ and $R^3$ are alkyl or hydroxyalkyl radicals with 1-4 carbon atoms,
  $R^4$ is an alkyl radical with 1-18 carbon atoms or $R^2$ and $R^3$ together with the nitrogen atom form a ring substituted as in formula 2, where:
  W is a methylene group or an oxygen atom,
  U and T are methyl radicals or hydrogen atoms,
  Z is a hydrogen atom or T and Z together are an oxygen atom.

The agent containing an active compound with the general formula 1, where the substituents have the above meaning has strong fungicidal activity towards pathogenic fungi and bacteria, among which are fungi from the Alternaria genus.

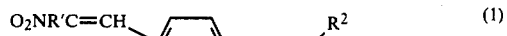

(1)

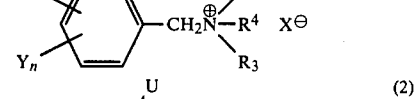

(2)

1 Claim, No Drawings

PARASTICIDE

This is a Divisional Application of Ser. No. 884,842, filed Mar. 9, 1978, now U.S. Pat. No. 4,217,365, issued Aug. 12, 1980.

This invention relates to a substance containing new active agents, for control of pathogens causing plant diseases.

Known is variety of substances for control of pathogens causing plant diseases.

Among others, commonly used are fungicides from the benzimidazole group. However, it has been stated repeated application of these effective, though very selective fungicides, causes changes in plant parasite microflora. Pathogens destroyed by benzimidazole derivatives are replaced by others, as fungi from the Alternaria genus, giving rise to arducus plant diseases.

Unexpectedly, it has been stated that underscribed until now substances with the general formula 1, where:
X is a halogen atom,
Y is a hydroxyl, alkoxyl, alkyl or nitro group and "n" is the number of Y substituents, and equals 0–4,
$R^1$ is an alkyl radical with 1–3 carbon atoms or a hydrogen atom,
$R^2$ and $R^3$ are alkyl or hydroxyalkyl radicals with 1–4 carbon atoms,
$R^4$ is an alkyl radical with 1–18 carbon atoms,
or
$R^2$ and $R^3$ together with the nitrogen atom form a ring substituted as in formula 2, where:
W is a methylene group or an oxygen atom,
U and T are methyl radicals or hydrogen atoms,
Z is a hydrogen atom,
or
T and Z together are an oxygen atom, plant

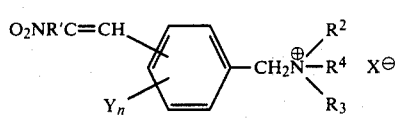
(1)

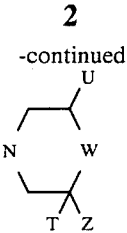
(2)

exhibit strong activity towards pathogens causing plant diseases.

The agent according to the present invention, containing an active compound with the general formula 1, where the substituents have above meaning, has strong fungicidal activity towards pathogenic fungi and bacteria, among which are fungi from the Alternaria genus.

Effectiveness of the agent according to the present invention towards the Alternaria, Botrytis, Rhizoctonia, Fusarium and Aspergillus genera was tested in comparison to known fungicides as carbendazime /2-benzimidazole-carbamic acid methyl ester/, methylthiophanate /1,2-bis/3-methoxycarbonyl-2-thioureido/-benzene/ and tridemorph /N-tridecyl-2,6-dimethylmorpholine/.

Effectiveness of compounds with the general formula 3, was tested in vitro on Alternaria tenuis spores from a 4-day culture and Botrytis cinerea spores from a 14-day culture. Results of investigations are given in table 1. As a measure of effectiveness was taken the lowest concentration. Completely inhibiting spore germination.

TABLE 1

Effectiveness of compounds with the general formula 3.

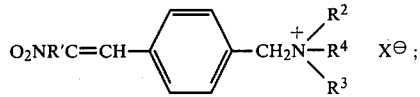
(3)

| No | $R^1$ | $R^2$ | $R^3$ | $R^4$ | X | Concentration inhibiting spore germination in ppm Alternaria tenuis | Botrytis cinerea |
|----|-------|-------|-------|-------|---|---------|---------|
| 1 | —CH₃ | —CH₃ | —CH₃ | —C₈H₁₇ | Br | >1000 | 1000 |
| 2 | —CH₃ | —CH₃ | —CH₃ | —C₁₀H₂₁ | Cl | ±1000 | 100 |
| 3 | —CH₃ | —CH₃ | —CH₃ | —C₁₂H₂₅ | Cl | 100 | <10>1 |
| 4 | —CH₃ | —CH₃ | —CH₂CH₂OH | —C₁₀H₂₁ | Cl | 100 | 100 |
| 5 | —CH₃ | —CH₃ | —CH₂CH₂OH | —C₁₂H₂₅ | Cl | 100 | <10>1 |
| 6 | —CH₃ | —CH₂CH₂O—CH₂CH₂— | | —C₇H₁₅ | J | >1000 | ±100 |
| 7 | —CH₃ | —CH₂CH₂—O—CH₂CH₂— | | —C₇H₁₅ | Cl | 1000 | 100 |
| 8 | —CH₃ | —CH₂CH₂—O—CH₂CH₂— | | —C₈H₁₇ | Cl | ±100 | 100 |
| 9 | —CH₃ | —CH₂CH₂—O—CH₂CH₂— | | —C₁₀H₂₁ | Cl | 100 | 100 |
| 10 | —CH₃ | —CH₂CH₂—O—CH₂CH₂— | | —C₁₂H₂₅ | Cl | 100 | ±10 |
| 11 | —CH₃ | —CH₂CH₂—O—CH₂CH₂— | | —C₁₄H₂₉ | Cl | 10 | <10>1 |
| 12 | —CH₃ | —CH₂CH—O—CH—CH₂ with CH₃ CH₃ | | —C₁₂H₂₅ | Cl | 100 | <10>1 |
| Carbendazime | | | | | | >1000 | ±10 |
| Methylthiophenate | | | | | | >1000 | ±10 |
| Tridemorph | | | | | | >1000 | >1000 |

Germination of Alternaria tenuis spores was inhibited already in concentrations of the compounds significantly lower than concentrations of reference fungicides: carbendazime, methylthiophanate, tridemorph. Especially effective was compound 11, which inhibited spore germination in concentrations 100 times lower than the known fungicides.

Germination of Botrytis cinerea spores was inhibited by lower concentrations of compounds 3, 5, 11, 12 and equal concentrations of compound 10 compared to carbendazime and methylthiophanate and in 100 times lower concentrations compared to tridemorph.

Effectiveness of compounds with the general formula 4 was tested similarly as for compounds with the general formula 3.

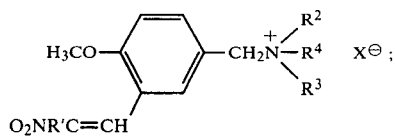
(4)

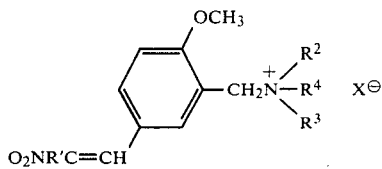
(5)

Results are given in table 3.

TABLE 3

Effectiveness of compounds with the general formula 5.

| | | | | | Concentration inhibiting germination of spores in ppm | |
|---|---|---|---|---|---|---|
| No | R$^1$ | R$^2$ | R$^3$ | R$^4$ | X | Alternaria tenuis | Botrytis cinerea |
| 26 | —CH$_3$ | —CH$_3$ | —CH$_3$ | —C$_7$H$_{15}$ | Br | 1000 | ±100 |
| 27 | —CH$_3$ | —CH$_3$ | —CH$_3$ | —C$_{10}$H$_{21}$ | Cl | ±100 | 100 |
| 28 | —CH$_3$ | —CH$_3$ | —CH$_3$ | —C$_{12}$H$_{25}$ | Cl | ±10 | <10>1 |
| 29 | —CH$_3$ | —CH$_3$ | —CH$_2$CH$_2$OH | —C$_8$H$_{17}$ | Cl | ±100 | 1000 |
| 30 | —CH$_3$ | —CH$_3$ | —CH$_2$CH$_2$OH | —C$_{10}$H$_{21}$ | Cl | ±1000 | ±10 |
| 31 | —CH$_3$ | —CH$_3$ | —CH$_2$CH$_2$OH | —C$_{12}$H$_{25}$ | Cl | ±100 | <10>1 |
| 32 | —CH$_3$ | —C$_2$H$_5$ | —CH$_2$CH$_2$OH | —C$_{10}$H$_{21}$ | Cl | 10 | ±10 |
| 33 | —CH$_3$ | —C$_2$H$_5$ | —CH$_2$CH$_2$OH | —C$_{12}$H$_{25}$ | Cl | <10>1 | <10>1 |
| 34 | —CH$_3$ | —CH$_2$—CH$_2$—O—CH$_2$CH$_2$— | | —C$_7$H$_{15}$ | J | >1000 | ±1000 |
| 35 | —CH$_3$ | —CH$_2$CH$_2$—O—CH$_2$CH$_2$— | | —C$_7$H$_{15}$ | Cl | >1000 | 1000 |
| 36 | —CH$_3$ | —CH$_2$CH$_2$—O—CH$_2$CH$_2$— | | —C$_8$H$_{17}$ | Cl | 100 | <10>1 |
| 37 | —CH$_3$ | —CH$_2$CH$_2$—O—CH$_2$CH$_2$— | | —C$_{10}$H$_{21}$ | Cl | ±100 | <10>1 |
| 38 | —CH$_3$ | —CH$_2$CH$_2$—O—CH$_2$CH$_2$— | | —C$_{12}$H$_{25}$ | Cl | 100 | <10>1 |
| 39 | —CH$_3$ | —CH$_2$CH—O—CHCH$_2$—<br>       \|              \|<br>       CH$_3$       CH$_3$ | | —C$_{12}$H$_{25}$ | Cl | 100 | <10>1 |
| Carbendazime | | | | | | >1000 | ±10 |
| Methylthiophanate | | | | | | >1000 | ±10 |
| Tridemorph | | | | | | >1000 | >1000 |

Most of the tested compounds was more effective towards Alternaria tenuis than the reference fungicides.

Results are given in Table 2.

TABLE 2

Effectiveness of compounds with the general formula 4.

| | | | | | Concentration inhibiting spore germination in ppm | |
|---|---|---|---|---|---|---|
| No | R$^1$ | R$^2$ | R$^3$ | R$^4$ | X | Alternaria tenuis | Botrytis cinerea |
| 13 | —CH$_3$ | —CH$_3$ | —CH$_3$ | —C$_8$H$_{17}$ | Br | >1000 | ±100 |
| 14 | —H | —CH$_3$ | —CH$_3$ | —C$_{10}$H$_{21}$ | Cl | 100 | <10>1 |
| 15 | —CH$_3$ | —CH$_3$ | —CH$_3$ | —C$_{10}$H$_{21}$ | Cl | ±1000 | <10>1 |
| 16 | —CH$_3$ | —CH$_3$ | —CH$_3$ | —C$_{12}$H$_{25}$ | Cl | 100 | <10>1 |
| 17 | —CH$_3$ | —CH$_3$ | —CH$_2$CH$_2$OH | —C$_{10}$H$_{21}$ | Cl | ±10 | <10>1 |
| 18 | —H | —CH$_3$ | —CH$_2$CH$_2$OH | —C$_{12}$H$_{25}$ | Cl | ±10 | <10>1 |
| 19 | —CH$_3$ | —C$_2$H$_5$ | —CH$_2$CH$_2$OH | —C$_{12}$H$_{25}$ | Cl | ±10 | ±10 |
| 20 | —CH$_3$ | —CH$_2$CH$_2$—O—CH$_2$CH$_2$— | | —C$_7$H$_{15}$ | Cl | 1000 | <10>1 |
| 21 | —CH$_3$ | —CH$_2$CH$_2$—O—CH$_2$CH$_2$— | | —C$_8$H$_{17}$ | Cl | 100 | <10>1 |
| 22 | —CH$_3$ | —CH$_2$CH$_2$—O—CH$_2$CH$_2$— | | —C$_{10}$H$_{21}$ | Cl | 100 | <10>1 |
| 23 | —CH$_3$ | —CH$_2$CH$_2$—O—CH$_2$CH$_2$— | | —C$_{12}$H$_{25}$ | Cl | <10>1 | <10>1 |
| 24 | —CH$_3$ | —CH$_2$CH$_2$—O—CH$_2$CH$_2$— | | —C$_{14}$H$_{29}$ | Cl | <10>1 | ±10 |
| 25 | —CH$_3$ | —CH$_2$CH$_2$—O—CH$_2$CH$_2$— | | —C$_{16}$H$_{33}$ | Cl | ±10 | ±10 |
| Carbendazime | | | | | | >1000 | ±10 |
| Methylthiophenate | | | | | | >1000 | ±10 |
| Tridemorph | | | | | | >1000 | >1000 |

Compounds 17, 18, 19, 24 and 25 were much more effective towards Alternaria tenuis than the reference fungicides. For Botrytis cinerea, most of the compounds are more effective than the reference fungicides.

Effectiveness of compounds with the general formula 5 was tested similarly as for compounds with the general formula 3.

Especially effective was compound No 32. Most of the tested compounds was more effective towards Botrytis cinerea than the reference fungicides.

Compounds described by the general formula 1 may be prepared by quarternation from R$^2$, R$^3$, R$^4$N tertiary amines, where R$^2$, R$^3$ and R$^4$ have the above meaning, with appropriately substituted halogen methyl-β-nitro-β-alkyl styrenes or halogen methyl-β-nitro styrenes. Quarternation may be carried out in solution with solvents such as benzene, acetone, dimethylformamide or their mixtures. Most of the tertiary amines was prepared through alkylation of secondary amines by known methods; derivatives of 2-oxo-morpholine were obtained by alkylation and cyclization reactions of appropriate monoalkyl ethanolamines with chloracetic acid esters.

Compounds described by formula 1 may also be prepared by quaternation of appropriate N,N-dialkyl-/β-nitroalkenyl/-benzylamines with akyl halides. Compounds with the general formula 1 have typical chemical properties of quarternary ammonium salts and are soluble in water, thus their application is simplified.

The agent according to the present invention may be used as water solutions, wettable powders, concentrated powders for dusting, emulsions, pastes and tablets. To achieve this, the biologically active substance is mixed with appropriate mineral or organic carriers such as kaolin, synthetic or natural kieselguhr, bentonite, talc, grain flour, woodbark or walnut shell flour; thinners or solvents as water, methanol, ethanol, ethyleneglycol and surface-active agents, emulsifiers, dispersers and wetting agents as ammonium salts, alkali or alkaline earth metal salts, lignine sulphonic acids, alkyl or aryl sulphonic acids, alkyl or aryl sulphonic derivatives, derivatives of N-methyl-taurine or adducts of ethylene oxide to fatty alcohols, fatty acids or higher aromatic or aliphatic amines.

The final product may contain other additives as buffers, densifiers, adherents, antifoaming agents and colors.

The agent according to the present invention may be introduced into molded materials for encapsulation of seeds prepared for sowing. It may also be applied as an additive for paints, lacquers and other polymers for protection against destructive fungi.

An advantage of the agent according to the present invention is the simplicity of its application arising from solubility of the active compound in water along with higher effectiveness of some compounds in comparison to known and presently used fungicides. Good solubility in water simplifies assimilation by plants and enables systemic activity. Another advantage of the agent is its broad spectrum of activity towards pathogens, with effective inhibitive activity towards some bacteria.

EXAMPLE I 10 parts by weight of N-dodecyl-N-ethyl-N-/2-hydroxy-ethyl/-N-[2-methoxy-5-/β-nitro-β-methyl-vinylbenzyl] amine chloride with 0,3 parts by weight of alkylarylpolyglycol ether and 89,7 parts by weight of distilled water.

Prepared as in example I agent in the liquid form, tested in concentrations of the active compound from 1 to 10 ppm, very effectively inhibited germination of Alternaris tenuis and Botrytis cinerea spores.

EXAMPLE II 50 parts by weight of N-dodecyl-N-[3-/β-nitro-β-methyl-vinyl/-4-methoxy-benzyl]morpholine chloride mixed with 40% of mineral carrier /kieselguhr/, 2% of wetting agent +8% disperser/waste calcium sulphite liquor/.

Prepared as in example II wettable powder dissolved in water to obtain active compound concentrations of 1-10 ppm completely inhibited germination of Alternaris tenuis and Botrytis cinerea spores.

We claim:

1. A fungicidal composition containing as the active substance therein a fungicidally effective amount of a compound having the formula:

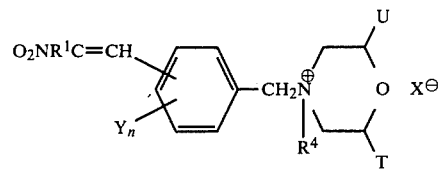

wherein
X is a halogen atom,
Y is a hydroxy or nitro group,
n is 0-4
$R^1$ is an alkyl radical with 1-3 carbon atoms or a hydrogen atom,
$R^4$ is an alkyl radical with 7-16 carbon atoms, and
U and T are methyl radicals or hydrogen atoms, and a carrier selected from the group consisting of kaolin, synthetic and natural kieselguhr, bentonite, talc, grain flour, woodbark and walnut shell flour.

* * * * *